US012668490B2

(12) United States Patent (10) Patent No.: US 12,668,490 B2
Lee et al. (45) Date of Patent: Jun. 30, 2026

(54) METHOD FOR PREPARING WHITLOCKITE, AND WHITLOCKITE PREPARED THEREBY

(71) Applicant: The Industry & Academic Cooperation in Chungnam National University (IAC), Daejeon (KR)

(72) Inventors: Jae Beom Lee, Hwaseong-si (KR); Ki Jae Jeong, Busan (KR); Cai Feng Wang, Daejeon (KR)

(73) Assignee: The Industry & Academic Corporation in Chungnam National University (IAC), Daejeon (KR)

( * ) Notice: Subject to any disclaimer, the term of this patent is extended or adjusted under 35 U.S.C. 154(b) by 965 days.

(21) Appl. No.: 17/779,475

(22) PCT Filed: Jul. 30, 2020

(86) PCT No.: PCT/KR2020/010098
§ 371 (c)(1),
(2) Date: May 24, 2022

(87) PCT Pub. No.: WO2021/107325
PCT Pub. Date: Jun. 3, 2021

(65) Prior Publication Data
US 2023/0002230 A1 Jan. 5, 2023

(30) Foreign Application Priority Data

Nov. 29, 2019 (KR) .......................... 10-20190156714
Jan. 13, 2020 (KR) ......................... 10-2020-0004080

(51) Int. Cl.
*C01B 25/32* (2006.01)
*A61F 2/28* (2006.01)

(52) U.S. Cl.
CPC ................ *C01B 25/32* (2013.01); *A61F 2/28* (2013.01)

(58) Field of Classification Search
CPC .... C01B 25/32; A61F 2/28; A61F 2002/2835; A61F 2310/00293; A61L 27/12
See application file for complete search history.

(56) References Cited

U.S. PATENT DOCUMENTS

2014/0161742 A1* 6/2014 Hong ..................... A61Q 11/00
424/52

FOREIGN PATENT DOCUMENTS

CN 101734639 A * 6/2010
JP 4522549 B2 8/2010
(Continued)

OTHER PUBLICATIONS

Machine translation of CN101734639A (Year: 2010).*
(Continued)

*Primary Examiner* — Anthony J Zimmer
*Assistant Examiner* — Logan Laclair
(74) *Attorney, Agent, or Firm* — STIP Law Group, LLC

(57) ABSTRACT

The present invention relates to a method for producing whitlockite, and whitlockite produced thereby. A method for producing whitlockite according to one embodiment of the present invention comprises: a step of preparing a precursor solution by mixing a first solution containing a calcium (Ca) ion source material, a second solution containing a magnesium (Mg) ion source material, and a third solution containing a phosphate ($PO_4$) source material; a heat-treatment step of heat-treating the precursor solution; and a step of separating and purifying the precipitate formed in the solution, after the heat-treatment step.

4 Claims, 3 Drawing Sheets

(56) References Cited

FOREIGN PATENT DOCUMENTS

| | | |
|---|---|---|
| KR | 20050021856 A | 3/2005 |
| KR | 20140020605 A | 2/2014 |
| KR | 20140075361 A | 6/2014 |
| KR | 20160080512 A | 7/2016 |
| KR | 20210128985 A | 10/2021 |

OTHER PUBLICATIONS

Zhou et al. (Comparative study of porous hydroxyapatite/chitosan and whitlockite/chitosan scaffolds for bone regeneration in calvarial defects, Int. J. of Nanomedicine, 2017) (Year: 2017).*

Wang et al. (Synthesis and formation mechanism of bone mineral, whitlockite nanocrystals in tri-solvent system, Journal of Colloid and Interface Science, 2020) (Year: 2020).*

International search report of PCT/KR2020/010098, Nov. 6, 2020, English translation.

Chucheng Lin et al, A rapid way to synthesize magnesium whitlockite microspheres for high efficiency removing heavy metals, Desalination and Water Treatment, September, vol. 162, pp. 220-227, Desalination Publications, Hopkinton, MA, USA.

Chao Qi et al, Magnesium whitlockite hollow microspheres: a comparison of microwave-hydrothermal and conventional hydrothermal syntheses using fructose 1,6-bisphosphate, and application in protein adsorption, RSC Advances, 2016, vol. 6, pp. 33393-33402, The Royal Society of Chemistry, London, United Kingdom.

Chao Qi et al, Porous microspheres of magnesium whitlockite and amorphous calcium magnesium phosphate: microwave-assisted rapid synthesis using creatine phosphate, and application in drug delivery, Journal of Materials Chemistry B, Nov. 14, 2015, pp. 1-12, he Royal Society of Chemistry, London, United Kingdom.

Mary Ann Liebert, Inc., Jung Yul Lim and Henry J. Donahue, Cell Sensing and Response to Micro- and Nanostructured Surfaces Produced by Chemical and Topographic Patterning, Tissue Engineering, 2007, vol. 13, No. 8, pp. 1879-1891, Larchmont, New York, United States.

Jeff S. Siber et al, Donor Site Morbidity After Anterior Iliac Crest Bone Harvest for Single-Level Anterior Cervical Discectomy and Fusion, Spine, 2003, vol. 28, No. 2, pp. 134-139, Lippincott Williams & Wilkins, Inc. Philadelphia, Pennsylvania, United States.

Frank, B. Bagambisa et al, Mechanisms and structure of the bond between bone and hydroxyapatite ceramics, Journal of Biomedical Materials Research, 1993, vol. 27, pp. 1047-1055, John Wiley & Sons, Inc. Hoboken, New Jersey, United States.

Nong-Soon Chang et al, Osteoconduction at porous hydroxyapatite with various pore configurations, Biomaterials, 2000, vol. 21, pp. 1291-1298, Elsevier Science Ltd., Amsterdam, Netherlands.

Jae Hyup Lee et al, A prospective consecutive study of instrumented posterolateral lumbar fusion using synthetic hydroxyapatite (Bongros1-HA) as a bone graft extender, Journal of Biomedical Materials Research Part A, 2008, pp. 804-810, Wiley Periodicals, Inc. Hoboken, New Jersey, United States.

* cited by examiner

[FIG. 1]
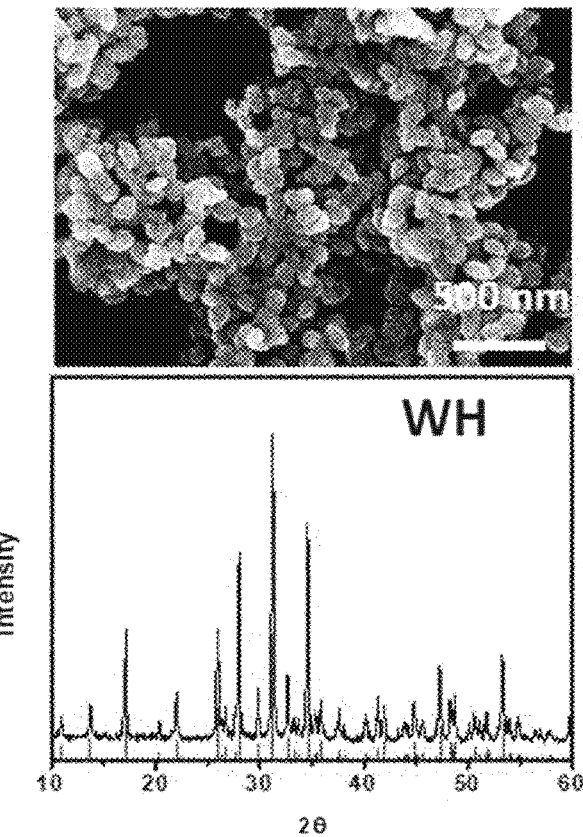
[FIG. 2]
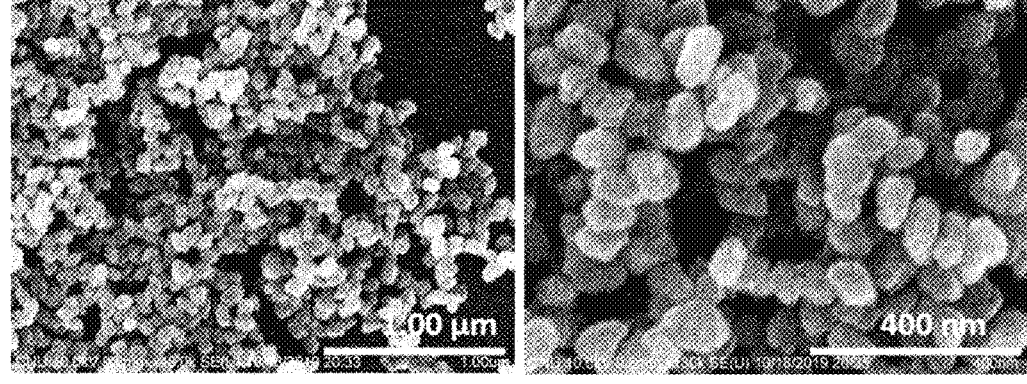

[FIG. 3]
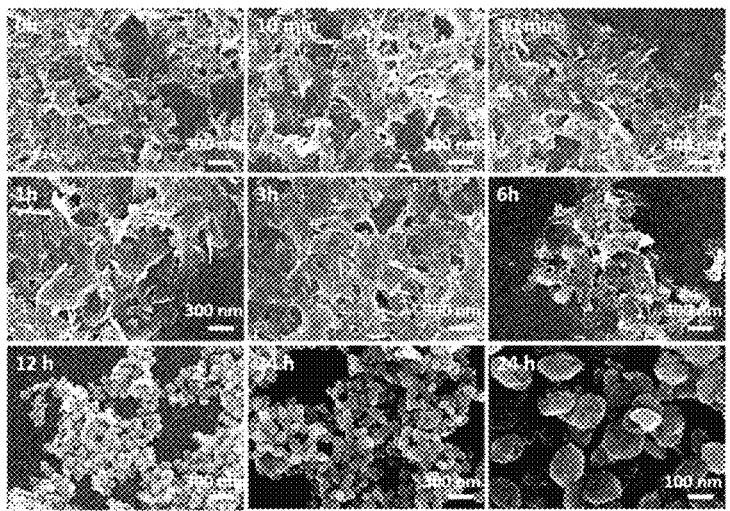
[FIG. 4]
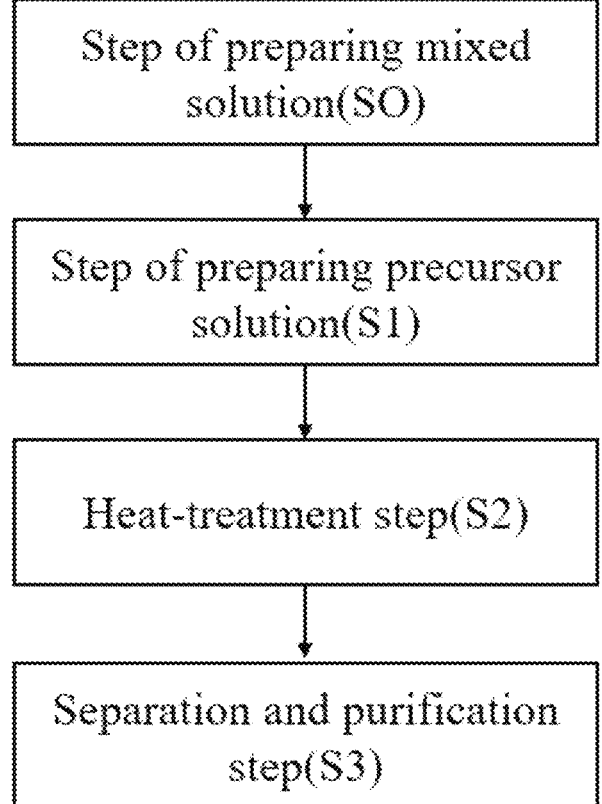

[FIG. 5]
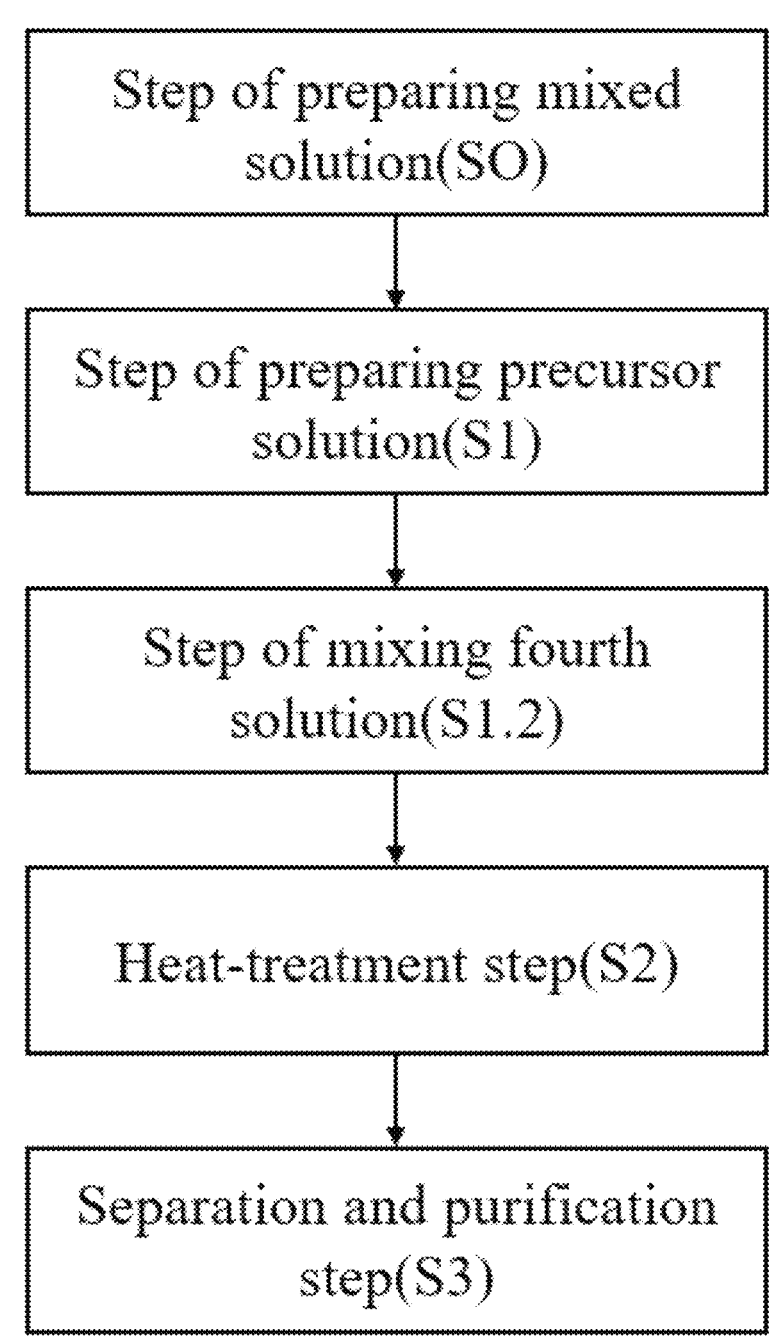

METHOD FOR PREPARING WHITLOCKITE, AND WHITLOCKITE PREPARED THEREBY

CROSS-REFERENCE TO RELATED APPLICATIONS

This application is the U.S. National Phase under 35 U.S.C. § 371 of International Application No. PCT/KR2020/010098 filed on Jul. 30, 2020, which in turn claims the benefit of Korean Application No. 10-2019-0156714 filed on Nov. 29, 2019, and Korean Application No. 10-2020-0004080 filed on Jan. 13, 2020, the disclosures of which are incorporated by reference into the present application.

TECHNICAL FIELD

The present invention relates to a method for producing whitlockite and whitlockite produced thereby. More particularly, the present invention provides a method for producing whitlockite, which is capable of producing whitlockite in large amounts by increasing the production efficiency of whitlockite, and whitlockite produced according to the production method.

BACKGROUND ART

In bone graft surgery, a method of grafting autogenous bone is usually used. However, this autologous bone grafting method has a problem in that it may involve complications such as pain at the donor site, infection, hematoma, and fracture. In particular, this method has a shortcoming in that it is difficult to obtain a sufficient amount of bone graft required to perform autologous bone grafting (Silber J S, Anderson D G, Daffner S D, Brislin B T, Leland J M, Hilibrand A S, et al. Donor site morbidity after anterior iliac crest bone harvest for single-level anterior cervical discectomy and fusion. Spine. 2003; 28(2):134-9). Meanwhile, allogeneic bone and xenogenic bone have been developed to overcome the shortcomings of autogenous bone, but are hardly comparable with autogenous bone due to their lower osteogenic ability than autogenous bone. In addition, they have a problem in that cross-infection or antigen-antibody reaction cannot be completely excluded.

In order to overcome these shortcomings, many studies on the development of artificial bone materials have been conducted. Among them, synthetic bioactive ceramics such as hydroxyapatite $(Ca_{10}(PO_4)_6(OH)_2$, hereinafter referred to as 'HAP') and beta tricalcium phosphate $(Ca_3(PO_4)_2$, hereinafter referred to as 'β-TCP') show excellent biocompatibility and bone conduction ability, and have already been widely used as bone graft replacement materials in clinical practice. In addition, biphasic calcium phosphate (BCP), which is a mixture of the above-described HAP and β-TCP, has excellent biocompatibility, osteoconductivity, and biodegradability, and thus has been extensively studied and reported (Bagambisa F B, Joos U, Schilli W. Mechanism and structure of the bond between bone and hydroxyapatite ceramics. J Biomed Mater Res 1993; 27:1047-1055. Bagambisa F B, Joos U, Schilli W. Mechanism and structure of the bond between bone and hydroxyapatite ceramics. J Biomed Mater Res 1993; 27:1047-1055).

Ceramics having a porous structure as described above have a large contact surface with blood flow when grafted in vivo compared to a dense form, and new blood vessels and surrounding bone tissue may easily grow thereon to improve the union rate (Chang B-S, Hong K-S, Youn H-J, Ryu H-S, Chung S-S, Park K-W. Osteoconduction at porous hydroxyapatite with various pore configurations. Biomaterials. 2000; 21(12):1291-8).

HAP is a major mineral that accounts for 60 to 70% of bone in vivo and constitutes bone in vivo through three-dimensional self-assembly alignment, and it has excellent biocompatibility and is capable of bonding directly with natural bone, and thus has been synthesized artificially in vitro and used as a bone graft material (Lee J H, Hwang C J, Song B W, Koo K H, Chang B S, Lee C K. A prospective consecutive study of instrumented posterolateral lumbar fusion using synthetic hydroxyapatite (Bongros-HA) as a bone graft extender. Journal of biomedical materials research Part A. 2009; 90(3):804-10).

However, the ultimate purpose of bone grafting is to replace the bone graft material with autologous bone, and externally synthesized HAP has a shortcoming in that it remains in vivo without being substantially degraded, which interferes with complete replacement with autologous bone.

On the other hand, although not being as biocompatible as HAP, β-TCP is known as a material that is easily degraded in vivo, and thus when it is grafted in vivo, it is gradually degraded and replaced with regenerated bone, but is absorbed excessively quickly and cannot serve as a support until natural bone is sufficiently regenerated (Lim J Y, Donahue H J. Cell sensing and response to micro- and nanostructured surfaces produced by chemical and topographic patterning. Tissue engineering. 2007; 13(8):1879-91).

Meanwhile, in bone and teeth in vivo, whitlockite $(Ca_{18}Mg_2(HPO_4)_2(PO_4)_{12}$, hereinafter referred to as 'WH'), which is a calcium phosphate compound in which a small amount of calcium is substituted with magnesium, exists in addition to HAP which is the major component. WH has been found in various tissues in the human body, such as bone and cartilage, gallstones or decayed teeth, calculus, tuberculosis tissue, intervertebral discs, aorta, and teeth that have not yet protruded, and is widely distributed in normal and pathological tissues in the human body.

To commemorate the discovery of TCP in phosphate rocks by mineralogist Whitlock in 1941 using X-ray diffraction, Frondel named TCP Whitlockite. Although the crystal discovered by Whitlock at that time was actually a material in which a small amount of $Ca^{2+}$ is substituted with $Mg^{2+}$, this name is still used.

Such whitlockite is known as a material suitable for bone or teeth in terms of its structure or composition. In addition, the Ca/P ratio of WH is about 1.43:1, which is closer to the Ca/P ratio of β-TCP (1.5:1) than to the Ca/P ratio of HAP (1.67:1), suggesting that WH has properties more similar to β-TCP than to HAP. In addition, when whitlockite and HAP are used in certain amounts, it may be more suitable for purposes such as repairing bone or tooth tissue of the human body.

Nevertheless, the utilization of WH was insignificant. This is because there was considerable difficulty in obtaining WH in high purity, even though experiments for synthesizing WH in various ways have been conducted in the prior art. In addition, when the synthesis of WH is performed according to a conventional method that makes it possible to obtain high-purity WH, a problem arises in that the actual production yield of WH is considerably low. Thus, according to the conventional art, there is a problem in that it is impossible to produce WH through mass production resulting from process scale-up.

Furthermore, in a certain case, when WH was produced, a certain amount of HAP was also produced, but it could not be adjusted within a certain range. Thus, when artificial bone composed of a mixture of WH and HAP is used, problems arise in that it is impossible to obtain a mixture of WH and HAP having an appropriate WH content for application to bone or teeth, and the produced WH and HAP have to be mixed and used within a certain ratio range.

Patent Document 1 (KR 10-2014-0020605 A) discloses a method for mass production of nano-sized high-purity whitlockite powder, which is capable of producing whitlockite without a high-temperature heat treatment process and a washing process and may achieve process simplification. Patent Document 1 has significance over other prior arts in that it achieves process simplification. However, when the process is scaled up according to the embodiment disclosed in Patent Document 1 beyond the small-scale process which is a lab-scale process, there is a problem in that it is difficult to obtain high-purity nanoparticles. That is, in the prior art, the process of obtaining high-purity whitlockite is complicated, and the amount of whitlockite obtained is very limited in spite of this complicated process. Therefore, it appears that Patent Document 1 mentions the possibility of mass production with the advantage that the process is simpler than other prior art. However, when process scale-up is applied to Patent Document 1, it is impossible to produce high-purity nanoparticles. Therefore, Patent Document 1 has a limitation in that industrially meaningful mass production is impossible.

Patent Document 2 (KR 10-2014-0020605 A) discloses whitlockite having a chemical formula of $Ca_{20-y}X_y(HPO_4)_2(PO_4)_{12}$ while presenting an oral composition. In addition, Patent Document 2 discloses as a specific example of producing whitlockite, in which a calcium ion source material is calcium hydroxide $(Ca(OH)_2)$, a cation (X) source material is magnesium hydroxide $(Mg(OH)_2)$, and a phosphate source material is phosphoric acid $(H_3PO_4)$, as in Patent Document 1, or in which a calcium ion source material is calcium nitrate $(Ca(NO_3)_2)$, a cation source material is magnesium nitrate $(Mg(NO_3)_2)$, and a phosphate source material is phosphoric acid $(H_3PO_4)$. However, according to the above example, it is possible to produce a small amount of whitlockite in a lab-scale process, but when the process is scaled up and applied to a mass-production process, a problem arises in that whitlockite is not produced, unlike the lab-scale experiment.

Patent Document 3 (JP 4522549 B1) discloses mixing calcium hydrogen phosphate $(CaHPO_4)$ with calcium hydroxide and magnesium hydroxide while disclosing a process for producing whitlockite. However, the process according to Patent Document 3 is not only disadvantageous in terms of the purity and crystalline form of the produced whitlockite, but also applied only to small-scale production, and when the process is scaled up and applied to mass production, a problem arises in that whitlockite is not produced, unlike the lab-scale experiment.

PRIOR ART DOCUMENTS

Patent Documents (Patent Document 1) KR 10-2014-0020605 A (Patent Document 2) KR 10-2014-0020605 A (Patent Document 3) JP 4522549 B1

(Patent Document 4) KR 10-2016-0080512 A

DISCLOSURE

Technical Problem

An object of the present invention is to provide a method for producing whitlockite, which is capable of producing high-purity whitlockite while simplifying the process.

Another object of the present invention is to provide a method for producing whitlockite, which may be applied to a scaled-up process for industrially meaningful mass production.

Still another object of the present invention is to provide a method for producing a mixture of whitlockite and hydroxyapatite, which is capable of controlling the mixing ratio between whitlockite and hydroxyapatite (HAP).

Yet another object of the present invention is to provide whitlockite or a mixture of whitlockite and hydroxyapatite.

Technical Solution

To achieve the above objects, a method for producing whitlockite according to one embodiment of the present invention comprises: a step of preparing a precursor solution by mixing a first solution containing a calcium (Ca) ion source material, a second solution containing a magnesium (Mg) ion source material, and a third solution containing a phosphate $(PO_4)$ source material; a heat-treatment step of heat-treating the precursor solution; and a step of separating and purifying a precipitate formed in the solution, after the heat-treatment step.

In the method for producing whitlockite, the calcium ion source material may be any one selected from the group consisting of calcium hypochlorite, calcium perchlorate, calcium bromide, calcium iodide, calcium nitrate, calcium chloride, calcium acetate, and mixtures thereof.

In the method for producing whitlockite, the magnesium ion source material may be any one selected from the group consisting of magnesium perchlorate, magnesium bromide, magnesium chloride, magnesium sulfide, magnesium nitrate, magnesium acetate, and mixtures thereof.

In the method for producing whitlockite, the phosphate source material may further comprise any one selected from the group consisting of calcium phosphate, calcium metaphosphate, potassium phosphate, potassium dihydrogen phosphate, sodium phosphate, sodium hydrogen phosphate, magnesium phosphate, magnesium hydrogen phosphate, and mixtures thereof.

In the method for producing whitlockite, the step of preparing a precursor solution may comprise preparing a mixed solution by mixing the first solution with the second solution, and then mixing the third solution with the mixed solution.

In the method for producing whitlockite, the step of preparing a precursor solution may comprise mixing the first solution, the second solution and the third solution together simultaneously.

In the method for producing whitlockite, the calcium ion source material and the magnesium ion source material may be mixed together such that the molar ratio between $Ca^{2+}$ and $Mg^{2+}$ may be 10:1 to 1:4.

A method for producing a mixture of whitlockite and hydroxyapatite according to another embodiment of the present invention may comprise: a step of preparing a precursor solution by mixing a first solution containing a calcium (Ca) ion source material, a second solution containing a magnesium (Mg) ion source material, and a third solution containing a phosphate ($PO_4$) source material; a step of mixing a fourth solution containing a phosphoric acid ($PO_4$) source material other than the third solution with the precursor solution; a heat-treatment step of heat-treating the precursor solution; and a step of separating and purifying a precipitate formed in the solution, after the heat-treatment step.

Whitlockite according to still another embodiment of the present invention may be produced by the method for producing whitlockite.

A mixture of whitlockite and hydroxyapatite according to yet another embodiment of the present invention may be produced by the method for producing a mixture of whitlockite and hydroxyapatite.

Hereinafter, the present invention will be described in more detail.

A method for producing whitlockite according to one embodiment of the present invention comprises: a step of preparing a precursor solution by mixing a first solution containing a calcium (Ca) ion source material, a second solution containing a magnesium (Mg) ion source material, and a third solution containing a phosphate ($PO_4$) source material; a heat-treatment step of heat-treating the precursor solution; and a step of separating and purifying a precipitate formed in the solution, after the heat-treatment step.

Whitlockite according to the present invention includes whitlockite nanocrystals. In addition, whitlockite according to the present invention may have one or more shapes selected from the group consisting of sphere, rod, plate, polygon, rice grain, and cubic shapes.

The solvent of the solution may be any one selected from the group consisting of water, an organic solvent, an acid-base inorganic solvent, and mixtures thereof. Preferably, the solvent may be any one selected from the group consisting of water, oleic acid, methanol, ethanol, and mixtures thereof.

Preferably, when the step of preparing a precursor solution comprises mixing the first to third solutions together simultaneously, the solvent of each of the solutions may be a mixed solvent obtained by adding 0.001 to 1 part by weight of oleic acid to 100 parts by weight of water. The use of the mixed solvent may be quite advantageous in terms of process simplification, because it makes it possible to produce whitlockite while mixing the solutions together simultaneously. In particular, it enables stable production yield to be maintained even in a scaled-up process.

The heat-treatment step plays an important role in stably producing and maintaining nanoparticles in high purity while synthesizing whitlockite. Meanwhile, in the prior art, a method of performing heat treatment at a relatively high temperature is used. However, when the method of performing heat treatment at a relatively high temperature is a small-scale process which is a lab-scale process, there is no particular problem in the formation and maintenance of whitlockite, but when the method is a scaled-up process, a problem arises in that whitlockite is not produced, or the crystallinity of whitlockite is greatly reduced, or other crystals such as hydroxyapatite are formed while particles become larger, unlike the small-scale production process. This is because large differences in heat dissipation, mixing of solutions, transport of raw material solutions, and the like occur in the scaled-up process. Thus, as the heat treatment temperature in the heat treatment process decreases, even the large-scale process may exhibit the same quality and yield as in the small-scale process.

The heat-treatment step may be performed at 30 to 150° C. Preferably, the heat-treatment step may be performed at 50 to 90° C. When the heat-treatment step in the production method according to the present invention is performed at a temperature within the above-described temperature range, high-purity whitlockite may be stably produced at a relatively low temperature, and in particular, the appearance, purity and yield of particles may be maintained without changes even in a scaled-up process.

Preferably, the heat-treatment step may be performed for 8 to 36 hours. If the heat-treatment step is performed for less than 8 hours in the above-described temperature range, a problem arises in that produced whitlockite is difficult to grow into regular particles. On the other hand, when the heat-treatment time exceeds 36 hours, a problem arises in that the shape and structure of particles are changed as the particles grow larger, and thus it is difficult to obtain whitlockite. In particular, as the scale of the process increases, the quality and yield of whitlockite may significantly change depending on the heat-treatment time.

More preferably, the heat-treatment step may be performed for 12 to 24 hours. When the heat-treatment time is within the above range, it is possible to produce whitlockite having a uniform shape and high stability in a certain yield even when a scaled-up process is applied.

In the method for producing whitlockite, the calcium ion source material may be any one selected from the group consisting of calcium hypochlorite, calcium perchlorate, calcium bromide, calcium iodide, calcium nitrate, calcium chloride, calcium acetate, and mixtures thereof.

Preferably, the calcium ion source material may be calcium chloride. When calcium chloride is used, a stable reaction may be exhibited even in a large-scale process at low temperature, and considerable simplification of the process of mixing the solutions may also be achieved. In particular, the use of calcium chloride has an advantage over the use of calcium hydroxide or other calcium ion source materials in that the particle shape, purity and yield of whitlockite are significantly increased.

In the method for producing whitlockite, the magnesium ion source material may be any one selected from the group consisting of magnesium perchlorate, magnesium bromide, magnesium chloride, magnesium sulfide, magnesium nitrate, magnesium acetate, and mixtures thereof.

Preferably, the magnesium ion source material may be magnesium chloride. When magnesium chloride is used, a stable reaction may be exhibited even in a large-scale process at low temperature, and considerable simplification of the process of mixing the solutions may also be achieved. In particular, the use of magnesium chloride has an advantage over the use of magnesium hydroxide or other magnesium ion source materials in that the particle shape, purity and yield of whitlockite are significantly increased.

In the method for producing whitlockite, the phosphate source material may further comprise any one selected from the group consisting of calcium phosphate, calcium metaphosphate, potassium phosphate, potassium dihydrogen phosphate, sodium phosphate, sodium hydrogen phosphate, magnesium phosphate, magnesium hydrogen phosphate, and mixtures thereof.

Preferably, the phosphate source material in the third solution may be sodium hydrogen phosphate. When sodium hydrogen phosphate is used, a stable reaction may be exhibited even in a large-scale process at low temperature, and considerable simplification of the process of mixing the solutions may also be achieved. In particular, if a phosphate source material other than sodium hydrogen phosphate is used, an effective reaction does not proceed in a scaled-up process, and thus whitlockite having a certain purity and particle shape may not be produced in the scaled-up process. Specifically, if phosphoric acid is used, a problem arises in that whitlockite having a certain purity and particle shape may not be produced when the process is scaled up beyond a lab-scale experimental process of producing whitlockite in μg to mg scale. Thus, if phosphoric acid is used, a problem arises in industrially meaningful mass production is practically impossible. In addition, if calcium phosphate, calcium metaphosphate, potassium phosphate, potassium dihydrogen phosphate, monobasic sodium phosphate, magnesium phosphate, or magnesium hydrogen phosphate is used, whitlockite having a certain purity and particle shape may not be produced in a mass production process which is beyond a small-scale process, similar to the use of phosphoric acid.

However, when sodium hydrogen phosphate is used, the shape, purity and yield of whitlockite may be maintained without changes even in the process of producing whitlockite in kg scale. Thus, when whitlockite is produced by a mass production process, it is most preferable to use sodium hydrogen phosphate.

In the method for producing whitlockite, the step of preparing a precursor solution may comprise preparing a mixed solution by mixing the first solution with the second solution, and then mixing the third solution with the mixed solution.

When the third solution is mixed with the mixture of the first solution and the second solution as described above, it is possible to produce whitlockite using more various calcium ion source materials, magnesium ion source materials and phosphate source materials.

Preferably, the step of preparing a precursor solution may comprise preparing a mixed solution by mixing the first solution and the second solution, and then adding the mixed solution dropwise to the third solution.

Conversely, when a certain amount of phosphoric acid is added dropwise to the mixture of the calcium ion source material and the magnesium ion source material, types of compounds that may be used as the calcium ion source material, the magnesium ion source material and the phosphate source material may be relatively diverse. However, if the process is scaled up to a certain level or higher, a problem arises in that the purity or particle shape and yield of whitlockite are greatly reduced.

However, in the case in which the mixture of the calcium ion source material and the magnesium ion source material is added dropwise to the phosphate source material as described above, compounds that may be used as the calcium ion source material, the magnesium ion source material and the phosphate source material are limited, but there is an advantage in that the purity or particle shape and yield of the produced whitlockite may be maintained even when the process is scaled up. Thus, this case may be suitable for industrially meaningful mass production.

In the method for producing whitlockite, the step of preparing a precursor solution may comprise mixing the first solution, the second solution and the third solution together simultaneously.

When the solutions are mixed together simultaneously as described above, there is an advantage in that the process efficiency is increased due to simplification of the process. In particular, when this mixing method is applied to a large-scale process, the advantage becomes greater. However, a problem arises in that the types of calcium ion source material, magnesium ion source material and phosphate source material that may be used are limited. For example, if calcium hydroxide, magnesium hydroxide and phosphoric acid are mixed together, a problem arises in that whitlockite cannot be produced by the above-described process because the reaction occurs rapidly. In addition, a problem arises in that it is more difficult to produce whitlockite not only in a large-scale process but also in a small-scale process.

Preferably, when the first solution, the second solution and the third solution are mixed together simultaneously, the calcium ion source material may be calcium chloride, the magnesium ion source material may be magnesium chloride, the phosphate source material may be sodium hydrogen phosphate, and the process may be applied to a large-scale process which is a scaled-up process. In this case, it is possible to scale-up the process and to effectively produce whitlockite having an excellent purity, appearance and yield in an environment in which the materials come into contact and react with one another.

Preferably, a method for producing whitlockite according to one embodiment of the present invention may comprise: a step of preparing a mixed solution by mixing a first solution containing a calcium (Ca) ion source material and a second solution containing a magnesium (Mg) ion source material; a step of preparing a precursor solution by adding and mixing the mixed solution with a third solution containing a phosphoric acid ($PO_4$) source material; a heat-treatment step of heat-treating the precursor solution; and a step of separating and purifying a precipitate formed in the solution, after the heat-treatment step.

In the method for producing whitlockite, the calcium ion source material and the magnesium ion source material may be mixed together such that the molar ratio between $Ca^{2+}$ and $Mg^{2+}$ may be 10:1 to 1:4.

If the molar ratio is out of the above-described range, a problem arises in that whitlockite is not produced, but newberyite, hydroxyapatite, etc. are produced, or newberyite, hydroxyapatite, brushite, etc. are produced together with whitlockite in uncontrollable amounts. Thus, if the molar ratio is out of the above-described range, a problem arises in that it is impossible to produce high-purity whitlockite.

Preferably, the calcium ion source material and the magnesium ion source material may be mixed together such that the molar ratio between $Ca^{2+}$ and $Mg^{2+}$ may be 7.34:1 to 1:2. In this range, it is possible to produce high-purity whitlockite.

More preferably, the molar ratio may be 2:1 to 1:1.5. In this range, it is possible to produce high-purity whitlockite in a scale-up process.

A method for producing a mixture of whitlockite and hydroxyapatite according to another embodiment of the present invention may comprise: a step of preparing a precursor solution by mixing a first solution containing a calcium (Ca) ion source material, a second solution containing a magnesium (Mg) ion source material, and a third solution containing a phosphate ($PO_4$) source material; a step of mixing a fourth solution containing a phosphoric acid ($PO_4$) source material other than the third solution with the precursor solution; a heat-treatment step of heat-treating the precursor solution; and a step of separating and purifying a precipitate formed in the solution, after the heat-treatment step.

Preferably, the method for producing a mixture of whitlockite and hydroxyapatite according to another embodiment of the present invention comprises: a step of preparing a mixed solution by mixing a first solution containing a calcium (Ca) ion source material and a second solution containing a magnesium (Mg) ion source material; a step of preparing a precursor solution by adding and mixing the mixed solution with a third solution containing a phosphoric acid ($PO_4$) source material; a step of mixing a fourth solution containing a phosphoric acid ($PO_4$) source material other than the third solution with the precursor solution; a heat-treatment step of heat-treating the precursor solution; and a step of separating and purifying a precipitate formed in the solution, after the heat-treatment step.

In general, in the process of producing whitlockite, there is a case where hydroxyapatite and brushite are produced together with whitlockite in unpredictable amounts. In this case, the purity of whitlockite is lowered, and the contents of hydroxyapatite and brushite produced together with whitlockite cannot be predicted. Thus, if hydroxyapatite and the like are produced together with whitlockite in unpredictable amounts as described above, they are simply classified as low-purity whitlockite, and a problem arises in that the above product cannot be used for a specific purpose.

On the other hand, as an artificial bone material, a mixture obtained by mixing whitlockite and hydroxyapatite at a certain ratio is used in many cases. In these cases, a mixture obtained by mixing high-purity whitlockite and high-purity hydroxyapatite at a certain ratio is used.

Therefore, when the ratio between whitlockite and hydroxyapatite that are produced in the synthesis step is artificially adjusted or controlled, there is an advantage in that design may be made such that whitlockite and hydroxyapatite may be synthesized at a certain ratio and then immediately used as an artificial bone material. In particular, when whitlockite and hydroxyapatite are produced at a certain ratio in the synthesis step, there is an advantage in that the stability of the particles and the stability of the structure are excellent.

In the method for producing a mixture of whitlockite and hydroxyapatite, the calcium ion source material may be any one selected from the group consisting of calcium hypochlorite, calcium perchlorate, calcium bromide, calcium iodide, calcium nitrate, calcium chloride, calcium acetate, and mixtures thereof.

In the method for producing a mixture of whitlockite and hydroxyapatite, the magnesium ion source material may be any one selected from the group consisting of magnesium perchlorate, magnesium bromide, magnesium chloride, magnesium sulfide, magnesium nitrate, magnesium acetate, and mixtures thereof.

In the method for producing a mixture of whitlockite and hydroxyapatite, the phosphate source material may further comprise any one selected from the group consisting of calcium phosphate, calcium metaphosphate, potassium phosphate, potassium dihydrogen phosphate, sodium phosphate, sodium hydrogen phosphate, magnesium phosphate, magnesium hydrogen phosphate, and mixtures thereof.

Preferably, the phosphoric acid contained in the fourth solution may be trisodium phosphate. Trisodium phosphate may be used to produce hydroxyapatite.

When trisodium phosphate is used, hydroxyapatite crystals may be produced. That is, whitlockite is produced by the third solution, and hydroxyapatite is produced by the fourth solution. Accordingly, the content of each particle phase in the mixture of whitlockite and hydroxyapatite may be controlled by adjusting the molar ratio between the third solution and the fourth solution that are mixed together.

In the method for producing a mixture of whitlockite and hydroxyapatite, the step of preparing a precursor solution may comprise may comprise preparing a mixed solution by mixing the first solution with the second solution, and then mixing the third solution with the mixed solution. The sequential mixing method described above may be suitable for the purpose of small-scale production.

In the method for producing a mixture of whitlockite and hydroxyapatite, the step of preparing a precursor solution may comprise mixing the first solution, the second solution and the third solution together simultaneously.

In the production method in which the solutions are mixed together simultaneously as described above, there is an advantage in that the process efficiency is increased due to simplification of the process. In particular, when this mixing method is applied to a large-scale process, the advantage becomes greater. However, a problem arises in that the types of calcium ion source material, magnesium ion source material and phosphate source material that may be used are limited. For example, if calcium hydroxide, magnesium hydroxide and phosphoric acid are mixed together, a problem arises in that whitlockite cannot be produced by the above-described process because the reaction occurs rapidly.

Preferably, when the first solution, the second solution and the third solution are mixed together simultaneously, the calcium ion source material may be calcium chloride, the magnesium ion source material may be magnesium chloride, the phosphate source material contained in the third solution may be sodium hydrogen phosphate, the phosphate source material contained in the fourth solution may be trisodium phosphate, and the process may be applied to a large-scale process which is a scaled-up process.

In the method for producing a mixture of whitlockite and hydroxyapatite, the calcium ion source material and the magnesium ion source material may be mixed together such that the molar ratio between $Ca^{2+}$ and $Mg^{2+}$ may be 10:1 to 1:4.

Whitlockite according to still another embodiment of the present invention may be produced by the method for producing whitlockite.

A mixture of whitlockite and hydroxyapatite according to yet another embodiment of the present invention may be produced by the method for producing a mixture of whitlockite and hydroxyapatite.

Advantageous Effects

According to the method for producing whitlockite according to the present invention, it is possible to easily produce high-purity whitlockite while significantly simplifying the process.

The method for producing whitlockite according to the present invention may be applied to a scaled-up process, and may be applied to industrially meaningful mass production. Thus, industrially meaningful mass production of whitlockite is possible.

According to the method for producing a mixture of whitlockite according to the present invention, it is possible to produce a mixture of whitlockite and hydroxyapatite while controlling the mixing ratio between whitlockite and hydroxyapatite (HAP).

The method for producing whitlockite according to the present invention provides whitlockite or a mixture of whitlockite and hydroxyapatite whose contents have been artificially adjusted or controlled.

BRIEF DESCRIPTION OF DRAWINGS

FIG. 1 relates to whitlockite produced according to one embodiment of the present invention.

FIG. 2 relates to a method for producing whitlockite according to one embodiment of the present invention.

FIG. 3 relates to a method for producing whitlockite according to one embodiment of the present invention, and shows the time and the degree of crystal formation depending on time in the heat treatment step.

FIG. 4 relates to a flowchart showing a method for producing whitlockite according to one embodiment of the present invention.

FIG. 5 relates to a flowchart showing a method for producing a mixture of whitlockite and hydroxyapatite according to one embodiment of the present invention.

BEST MODE

The present invention relates to a method for producing whitlockite and whitlockite produced thereby. More particularly, the present invention provides a method for producing whitlockite, which is capable of producing the whitlockite in large amounts by increasing the production efficiency of whitlockite, and whitlockite produced according to the production method.

Mode for Invention

Hereinafter, examples of the present invention will be described in detail so that those of ordinary skill in the art can easily carry out the present invention. However, the present invention may be embodied in a variety of different forms and is not limited to the examples described herein.

[Production Method: Production of Whitlockite]

1. S1 Small-Scale Precipitation (S1CP)

The reactor was configured to have such a size that the final product was obtained in mg scale. A solution containing a calcium ion source material was mixed with a solution containing a magnesium ion source material, and a solution containing a phosphate source material was added dropwise to the mixed solution for a predetermined period of time at predetermined intervals. Next, the resulting mixture was heat-treated with stirring, and then the precipitate was separated and purified, and then dried.

2. S2 Large-Scale Precipitation (S2CP)

The reactor was configured to have such a size that the final product was obtained in mg scale. A solution containing a calcium ion source material was mixed with a solution containing a magnesium ion source material, and the mixed solution was added dropwise to a solution containing a phosphate source material for a predetermined period of time at predetermined intervals. Next, the resulting mixture was heat-treated with stirring, and then the precipitate was separated and purified, and then dried.

3. S3 Large-Scale Precipitation (S3CP)

The reactor was configured to have such a size that the final product was obtained in kg scale. A solution containing a calcium ion source material, a solution containing a magnesium ion source material, and a solution containing a phosphate source material were mixed together. The mixture was heat-treated with stirring, and then the precipitate was separated and purified, and then dried.

4. L1 Large-Scale Precipitation (L1CP)

The reactor was configured to have such a size that the final product was obtained in kg scale. A solution containing a calcium ion source material was mixed with a solution containing a magnesium ion source material, and a solution containing a phosphate source material was added dropwise to the mixed solution for a predetermined period of time at predetermined intervals. Next, the resulting mixture was heat-treated with stirring, and then the precipitate was separated and purified, and then dried.

5. L2 Large-Scale Precipitation (L2CP)

The reactor was configured to have such a size that the final product was obtained in kg scale. A solution containing a calcium ion source material was mixed with a solution containing a magnesium ion source material, and the mixed solution was added dropwise to a solution containing a phosphate source material for a predetermined period of time at predetermined intervals. Next, the resulting mixture was heat-treated with stirring, and then the precipitate was separated and purified, and then dried.

6. L3 large-scale precipitation (L3CP)

The reactor was configured to have such a size that the final product was obtained in kg scale. A solution containing a calcium ion source material, a solution containing a magnesium ion source material, and a solution containing a phosphate source material are mixed together. Next, the mixture was heat-treated with stirring, and then the precipitate was separated and purified, and then dried.

Production Example 1: Small-Scale Precipitation

1. S1CP-1

The materials shown in Table 1 below were used according to S1CP. Heat treatment was performed at a temperature of 80° C. for 12 hours.

TABLE 1

| Material | Raw material and molar concentration used |
|---|---|
| Calcium ion source material | $Ca(OH)_2$ 0.4M |
| Magnesium ion source material | $Mg(OH)_2$ 0.12M |
| Phosphate source material | $H_3PO_4$ 0.5M |

2. S1CP-2

The materials shown in Table 2 below were used according to S1CP. Heat treatment was performed at a temperature of 80° C. for 12 hours.

TABLE 2

| Material | Raw material and molar concentration used |
|---|---|
| Calcium ion source material | $Ca(OH)_2$ 0.4M |
| Magnesium ion source material | $Mg(OH)_2$ 0.12M |
| Phosphate source material | $CaHPO_4$ 0.5M |

3. S1CP-3

The materials shown in Table 3 below were used according to S1CP. Heat treatment was performed at a temperature of 80° C. for 12 hours.

TABLE 3

| Material | Raw material and molar concentration used |
|---|---|
| Calcium ion source material | $CaCl_2$ 0.4M |
| Magnesium ion source material | MgCl2 0.1M |
| Phosphate source material | $Na_2HPO_4$ 0.1M |

4. S1CP-4

The materials shown in Table 4 below were used according to S1CP. Heat treatment was performed at a temperature of 80° C. for 12 hours.

TABLE 4

| Material | Raw material and molar concentration used |
| --- | --- |
| Calcium ion source material | $Ca(NO_3)_2$ 0.4M |
| Magnesium ion source material | $Mg(NO_3)_2$ 0.1M |
| Phosphate source material | $Na_2HPO_4$ 0.5M |

5. S1CP-5

The materials shown in Table 5 below were used according to S1CP. Heat treatment was performed at a temperature of 80° C. for 12 hours.

TABLE 5

| Material | Raw material and molar concentration used |
| --- | --- |
| Calcium ion source material | $CaCl_2$ 0.4M |
| Magnesium ion source material | $MgCl_2$ 0.1M |
| Phosphate source material | $NaH_2PO_4$ 0.5M |

6. S1CP-6

The materials shown in Table 6 below were used according to S1CP. Heat treatment was performed at a temperature of 80° C. for 12 hours.

TABLE 6

| Material | Raw material and molar concentration used |
| --- | --- |
| Calcium ion source material | $CaCl_2$ 0.4M |
| Magnesium ion source material | $MgCl_2$ 0.1M |
| Phosphate source material | $Na_3PO_4$ 0.5M |

7. S1CP-7

The materials shown in Table 7 below were used according to S1CP. Heat treatment was performed at a temperature of 80° C. for 12 hours.

TABLE 7

| Material | Raw material and molar concentration used |
| --- | --- |
| Calcium ion source material | $Ca(OH)_2$ 0.4M |
| Magnesium ion source material | $Mg(OH)_2$ 0.12M |
| Phosphate source material | $Mg_3(PO_4)_2$ 0.5M |

8. S2CP-1

The materials shown in Table 8 below were used according to S2CP. Heat treatment was performed at a temperature of 80° C. for 12 hours.

TABLE 8

| Material | Raw material and molar concentration used |
| --- | --- |
| Calcium ion source material | $Ca(OH)_2$ 0.4M |
| Magnesium ion source material | $Mg(OH)_2$ 0.12M |
| Phosphate source material | $H_3PO_4$ 0.5M |

9. S2CP-2

The materials shown in Table 9 below were used according to S2CP. Heat treatment was performed at a temperature of 80° C. for 12 hours.

TABLE 9

| Material | Raw material and molar concentration used |
| --- | --- |
| Calcium ion source material | $Ca(OH)_2$ 0.4M |
| Magnesium ion source material | $Mg(OH)_2$ 0.12M |
| Phosphate source material | $CaHPO_4$ 0.5M |

10. S2CP-3

The materials shown in Table 10 below were used according to S2CP. Heat treatment was performed at a temperature of 80° C. for 12 hours.

TABLE 10

| Material | Raw material and molar concentration used |
| --- | --- |
| Calcium ion source material | $CaCl_2$ 0.1M |
| Magnesium ion source material | $MgCl_2$ 0.1M |
| Phosphate source material | $Na_2HPO_4$ 0.1M |

11. S2CP-4

The materials shown in Table 11 below were used according to S2CP. Heat treatment was performed at a temperature of 80° C. for 12 hours.

TABLE 11

| Material | Raw material and molar concentration used |
| --- | --- |
| Calcium ion source material | $CaCl_2$ 0.4M |
| Magnesium ion source material | $MgCl_2$ 0.12M |
| Phosphate source material | $NaH_2PO_4$ 0.5M |

12. S3CP-1

The materials shown in Table 12 below were used according to S3CP. Heat treatment was performed at a temperature of 80° C. for 12 hours.

TABLE 12

| Material | Raw material and molar concentration used |
| --- | --- |
| Calcium ion source material | $Ca(OH)_2$ 0.4M |
| Magnesium ion source material | $Mg(OH)_2$ 0.12M |
| Phosphate source material | $H_3PO_4$ 0.5M |

13. S3CP-2

The materials shown in Table 13 below were used according to S3CP. Heat treatment was performed at a temperature of 80° C. for 12 hours.

TABLE 13

| Material | Raw material and molar concentration used |
| --- | --- |
| Calcium ion source material | $Ca(OH)_2$ 0.4M |
| Magnesium ion source material | $Mg(OH)_2$ 0.12M |
| Phosphate source material | $CaHPO_4$ 0.5M |

14. S3CP-3

The materials shown in Table 14 below were used according to S3CP. Heat treatment was performed at a temperature of 80° C. for 12 hours.

TABLE 14

| Material | Raw material and molar concentration used |
|---|---|
| Calcium ion source material | $CaCl_2$ 0.1M |
| Magnesium ion source material | $MgCl_2$ 0.1M |
| Phosphate source material | $Na_2HPO_4$ 0.1M |

15. S3CP-4

The materials shown in Table 15 below were used according to S3CP. Heat treatment was performed at a temperature of 80° C. for 12 hours.

TABLE 15

| Material | Raw material and molar concentration used |
|---|---|
| Calcium ion source material | $Ca(NO_3)_2$ 0.4M |
| Magnesium ion source material | $Mg(NO_3)_2$ 0.1M |
| Phosphate source material | $Na_2HPO_4$ 0.5M |

Experimental Example 1: Results of WH Synthesis

The purity and particle phase of whitlockite for each product produced in the Production Example above were evaluated. For evaluation of each product produced in the Production Example, the case in which high-purity whitlockite that can be used industrially was produced was indicated by WH, and the case in which high-purity whitlockite was not produced due to problems such as purity and particle phase was indicated by X. The results are shown in Tables 16 and 17 below. Meanwhile, FIG. 1 relates to S1CP-3.

TABLE 16

| | S1CP-1 | S1CP-2 | S1CP-3 | S2CP-4 | S2CP-5 | S2CP-6 | S2CP-7 |
|---|---|---|---|---|---|---|---|
| Crystal phase | WH | WH | WH | WH | x | x | x |

TABLE 17

| | S2CP-1 | S2CP-2 | S2CP-3 | S2CP-4 | S3CP-1 | S3CP-2 | S3CP-3 | S3CP-4 |
|---|---|---|---|---|---|---|---|---|
| Crystal phase | x | x | WH | x | x | x | WH | x |

Referring to Table 16 above, it can be seen that, in the case of the small-scale process, more diverse materials could be used. It can be confirmed that, in the case of some compositions, the same whitlockite was not produced. In addition, referring to Table 17 above, it can be seen that, in the case of S2CP and S3CP in which process changes occurred and in the case of some compositions, whitlockite was not generated or problems in purity, shape and the like occurred. Meanwhile, FIG. 2 relates to S2CP-3.

However, referring to S2CP-3 and S3CP-3, it can be confirmed that the source materials had a relatively small effect on the reaction even when process changes occurred. Therefore, it can be seen that, in the case of the above compositions, not only simplification of the process is easily achieved, unlike in the case of other compositions, but also the possibility of mass production is high.

Production Example 2: Large-Scale Precipitation

1. L1CP-1

The materials shown in Table 18 below were used according to L1CP. Heat treatment was performed at a temperature of 80° C. for 24 hours.

TABLE 18

| Material | Raw material and molar concentration used |
|---|---|
| Calcium ion source material | $Ca(OH)_2$ 0.4M |
| Magnesium ion source material | $Mg(OH)_2$ 0.12M |
| Phosphate source material | $H_3PO_4$ 0.5M |

2. L1CP-2

The materials shown in Table 19 below were used according to L1CP. Heat treatment was performed at a temperature of 80° C. for 24 hours.

TABLE 19

| Material | Raw material and molar concentration used |
|---|---|
| Calcium ion source material | $Ca(OH)_2$ 0.4M |
| Magnesium ion source material | $Mg(OH)_2$ 0.12M |
| Phosphate source material | $CaHPO_4$ 0.5M |

3. L1CP-3

The materials shown in Table 20 below were used according to L1CP. Heat treatment was performed at a temperature of 80° C. for 24 hours.

TABLE 20

| Material | Raw material and molar concentration used |
|---|---|
| Calcium ion source material | $CaCl_2$ 0.1M |
| Magnesium ion source material | $MgCl_2$ 0.1M |
| Phosphate source material | $Na_2HPO_4$ 0.1M |

4. L1CP-4

The materials shown in Table 21 below were used according to L1CP. Heat treatment was performed at a temperature of 80° C. for 24 hours.

TABLE 21

| Material | Raw material and molar concentration used |
|---|---|
| Calcium ion source material | $Ca(NO_3)_2$ 0.4M |
| Magnesium ion source material | $Mg(NO_3)_2$ 0.1M |
| Phosphate source material | $Na_2HPO_4$ 0.5M |

5. L2CP-3

The materials shown in Table 22 below were used according to L2CP. Heat treatment was performed at a temperature of 80° C. for 24 hours.

TABLE 22

| Material | Raw material and molar concentration used |
|---|---|
| Calcium ion source material | $CaCl_2$ 0.1M |
| Magnesium ion source material | $MgCl_2$ 0.1M |
| Phosphate source material | $Na_2HPO_4$ 0.1M |

6. L3CP-3

The materials shown in Table 23 below were used according to L3CP. Heat treatment was performed at a temperature of 80° C. for 24 hours.

TABLE 23

| Material | Raw material and molar concentration used |
|---|---|
| Calcium ion source material | $CaCl_2$ 0.1M |
| Magnesium ion source material | $MgCl_2$ 0.1M |
| Phosphate source material | $Na_2HPO_4$ 0.1M |

Experimental Example 2: Results of WH Synthesis

Evaluation was performed in the same manner as in Experimental Example 1 above, and the results are shown in Table 24 below.

TABLE 24

| | L1CP-1 | L1CP-2 | L1CP-3 | L1CP-4 | L2CP-3 | L3CP-3 |
|---|---|---|---|---|---|---|
| Crystal phase | x | x | WH | x | WH | WH |

Referring to Table 24 above, it can be confirmed that, in the case of the L1 CP-1, L1 CP-2 and L1CP-3 compositions, whitlockite could not be produced. Thereby, it can be confirmed that, in the case of the L1CP-1, L 1 CP-2 and L 1 CP-3 compositions, it was difficult to perform process scale-up for mass production. Accordingly, the L2CP and L3CP processes did not need to be performed. On the other hand, it can be confirmed that, in the case of the L1CP-3 composition, whitlockite was produced in L 1 CP-3, L2CP-3, and L3CP-3. Therefore, it can be seen that, in the case of the above range, whitlockite could be mass-produced through the scale-up of the process.

In addition, the production yield was the highest in the case of L2CP-3, and L3CP-3 showed a yield similar to that of L1CP-1, but had excellent process efficiency due to process simplification. In particular, higher scale-up level may be more advantageous in terms of the process efficiency.

Specifically, L3CP-3 and L 1 CP-1 showed a production yield corresponding to about 70 to 80% of the production yield shown by L2CP-3. Meanwhile, L3CP-3 showed very higher process efficiency than L1CP-1. Specifically, for example, in the case of L3CP-3, the number of reactions can be reduced to half or less of that in L 1 CP-1, and the process may be performed using an in-line mixer or the like without a reactor due to the process of mixing the materials together simultaneously, unlike the case of L1CP-1 which necessarily requires a reactor. Thus, in the case of L3CP-3, it is possible to greatly reduce the process equipment, and the greater the size of the process, the greater the advantage.

Experimental Example 3: Experiment on WH Synthesis Conditions

To confirm the production yield of whitlockite depending on reaction conditions, the reactor was configured to have such a size that the final product was obtained in mg scale. According to Table 25 below, a solution containing a calcium ion source material was mixed with a solution containing a magnesium ion source material, and the mixed solution was added dropwise to a solution containing a phosphate source material for a predetermined period of time at predetermined intervals. Then, the resulting mixture was heat-treated with stirring, and then the precipitate was separated and purified, and then dried. Matters on whether or not whitlockite was produced under each condition are shown in Table 26 below.

Meanwhile, FIG. 3 relates to the crystal structure of whitlockite particles depending on time.

TABLE 25

| Material | Raw material used |
|---|---|
| Calcium ion source material | $CaCl_2$ |
| Magnesium ion source material | $MgCl_2$ |
| Phosphate source material | $Na_2HPO_4$ |

TABLE 26

| Example | Ca:Mg molar ratio | Temperature (° C.) | Time (hr) | Crystal phase |
|---|---|---|---|---|
| M1 | 9:1 | 90 | 24 | x |
| M2 | 7.34:1 | 90 | 24 | WH |
| M3 | 5.67:1 | 90 | 24 | WH |
| M4 | 4:1 | 90 | 24 | WH |
| M5 | 7:1 | 90 | 24 | WH |
| M6 | 1:1 | 90 | 24 | WH |
| M7 | 2.3:1 | 90 | 24 | x |
| M8 | 1:1 | 40 | 24 | x |
| M9 | 4:1 | 50 | 24 | WH |
| M10 | 4:1 | 60 | 24 | WH |
| M11 | 4:1 | 60 | 24 | WH |
| M12 | 4:1 | 70 | 24 | WH |
| M13 | 4:1 | 80 | 24 | WH |
| M14 | 4:1 | 90 | 24 | WH |

Production Example 3: Production of Mixture of WH and HAP

In order to produce a mixture of whitlockite and hydroxyapatite mixed together at an artificial ratio according to the control of a fourth solution, according to Table 27 below, a solution containing a calcium ion source material and a solution containing a magnesium ion source material were mixed together, and the mixed solution was added dropwise to a third solution containing a phosphate source material for a predetermined period of time at predetermined intervals.

Next, a fourth solution containing a phosphate source material was added dropwise to the mixed solution. The resulting mixture was heat-treated with stirring, and then the precipitate was separated and purified, and then dried.

TABLE 27

| Material | Raw material used |
| --- | --- |
| Calcium ion source material | $CaCl_2$ |
| Magnesium ion source material | $MgCl_2$ |
| Phosphate source material of third solution | $Na_2HPO_4$ |
| Phosphate source material of fourth solution | $Na_3PO_4$ |

From the above-described experimental results, it could be confirmed that a mixture of whitlockite and hydroxyapatite was produced, whitlockite was produced in proportion to the content of sodium hydrogen phosphate contained in the third solution, and hydroxyapatite was produced in proportion to the content of trisodium phosphate contained in the fourth solution. Therefore, it was confirmed that, according to the above-described method, it was possible to produce a mixture of whitlockite and hydroxyapatite in which the contents of the components were artificially designed/controlled/adjusted.

Although the preferred embodiments of the present invention have been described in detail above, the scope of the present invention is not limited thereto, and various modifications and improvements made by those skilled in the art without departing from the basic concept of the present invention as defined in the appended claims also fall within the scope of the present invention.

INDUSTRIAL APPLICABILITY

The present invention relates to a method for producing whitlockite and whitlockite produced thereby. More particularly, the present invention provides a method for producing whitlockite, which is capable of producing whitlockite in large amounts by increasing the production efficiency of whitlockite, and whitlockite produced according to the production method.

The invention claimed is:

1. A method for producing whitlockite comprising:
 (a) preparing a mixed solution by mixing a first solution containing calcium chloride with a second solution containing magnesium chloride;
 (b) preparing a precursor solution by adding the mixed solution dropwise to a third solution containing sodium hydrogen phosphate in a reactor configured to have such a size that whitlockite is obtained in kilogram scale;
 (c) heat-treating the precursor solution at 50° C. to 90° C. for 12 hours to 24 hours; and
 (d) separating and purifying a precipitate formed in the precursor solution after the heat-treatment step.

2. The method of claim 1, wherein the mixed solution is added dropwise to the third solution for a predetermined period of time at predetermined intervals.

3. The method of claim 1, wherein a solvent for at least one of the first solution, the second solution, and the third solution comprises water and oleic acid.

4. The method of claim 1, wherein the first solution and the second solution are mixed such that a molar ratio between $Ca^{2+}$ and $Mg^{2+}$ is 7.34:1 to 1:2.

* * * * *